US00PP19593P2

(12) United States Plant Patent
Kawashima et al.

(10) Patent No.: US PP19,593 P2
(45) Date of Patent: Dec. 23, 2008

(54) NEW GUINEA IMPATIENS PLANT NAMED 'SAKIMPO15'

(50) Latin Name: *Impatiens×hybrida*
Varietal Denomination: SAKIMP015

(75) Inventors: Moriya Kawashima, Yokohama (JP); Yoneo Kobayashi, Kakegawa (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 12/012,026

(22) Filed: Jan. 31, 2008

(51) Int. Cl.
*A01H 5/00* (2006.01)

(52) U.S. Cl. ..... Plt./318.3

(58) Field of Classification Search ..... Plt./318.3, Plt./318
See application file for complete search history.

*Primary Examiner*—Annette H Para
(74) *Attorney, Agent, or Firm*—Jondle & Associates, P.C.

(57) ABSTRACT

A New Guinea *Impatiens* cultivar particularly distinguished by having large, pinkish-orange flowers, large green leaves with yellow variegation, a compact plant habit, and strong rooting is disclosed.

1 Drawing Sheet

Genus and species: *Impatiens×hybrida.*
Variety denomination: 'SAKIMP015'.

BACKGROUND OF THE NEW PLANT

The present invention comprises of a new and distinct cultivar of New Guinea *Impatiens,* botanically known as *Impatiens×hybrida* (hort), and referred to by the variety name 'SAKIMP015'. 'SAKIMP015' originated from an interspecific hybridization between *Impatiens* 'NG-01H-9B', an unpatented proprietary pink-lilac flowered *Impatiens* breeding line and *Impatiens* 'NC-1H1', an unpatented proprietary light orange flowered *Impatiens* breeding line in Misato, Japan.

In January 2003, the female parent line 'NC-1H1' and male parent line 'NG-01H-9B' were crossed and a population of $F_1$ plants was created. The $F_1$ plants were evaluated in Misato, Japan in an open field trial. The criteria for plant selection included variegated leaves, strong root system and vigorous plant growth habit. At the completion of the trial, one single-plant selection was made based on the above criteria and vegetatively propagated. From May to August 2004, the selection was evaluated in an open field in Misato, Japan. Shoot-tip cuttings of the variety were then shipped to Salinas, Calif., where the plants were regenerated and reevaluated for stability of traits. The selection subsequently was named 'SAKIMP015' and found to have its unique characteristics reproduce true to type in successive generations of asexual propagation.

SUMMARY OF THE INVENTION

The following are the most outstanding and distinguishing characteristics of this new cultivar when grown under normal horticultural practices in Salinas, Calif.

1. Large, pinkish-orange flowers;
2. Large green leaves with yellow variegation;
2. Compact plant habit; and
3. Strong rooting.

DESCRIPTION OF THE PHOTOGRAPHS

This new *Impatiens* plant is illustrated by the accompanying photographs which show overall plant habit including blooms, buds, and foliage of the plant; the colors shown are as true as can be reasonably obtained by conventional photographic procedures. The photographs are of plants that are 5 months from their transplanting date and 6 months from the stick date.

DETAILED DESCRIPTION OF THE NEW CULTIVAR

Figure 1:
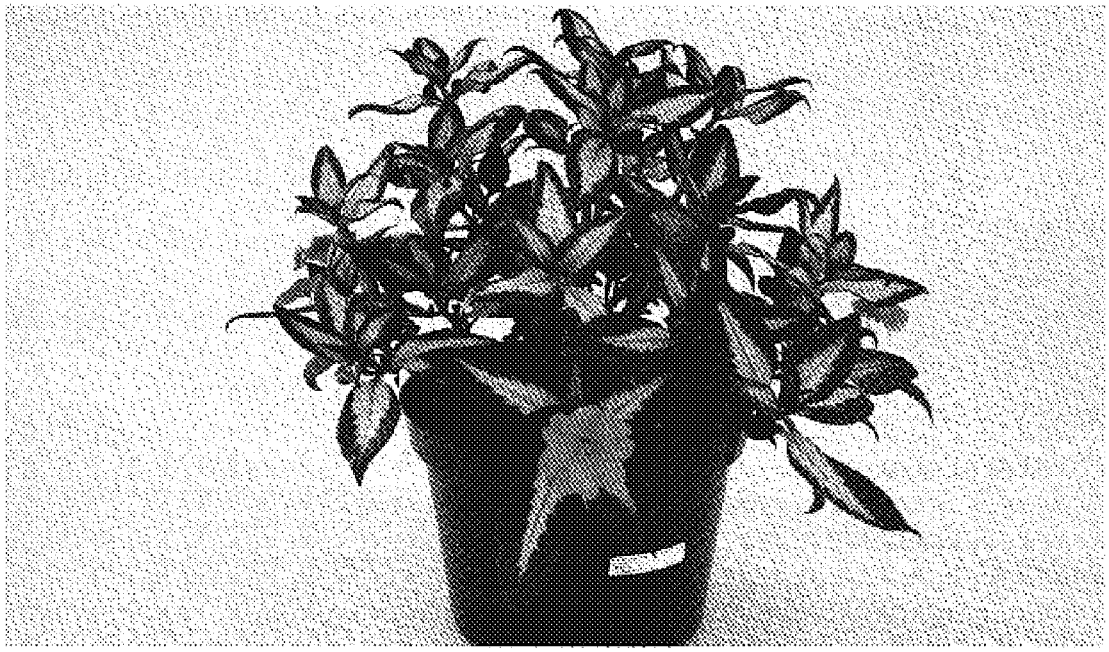
FIG. 1 shows overall plant habit including blooms, buds and foliage.
Figure 2:
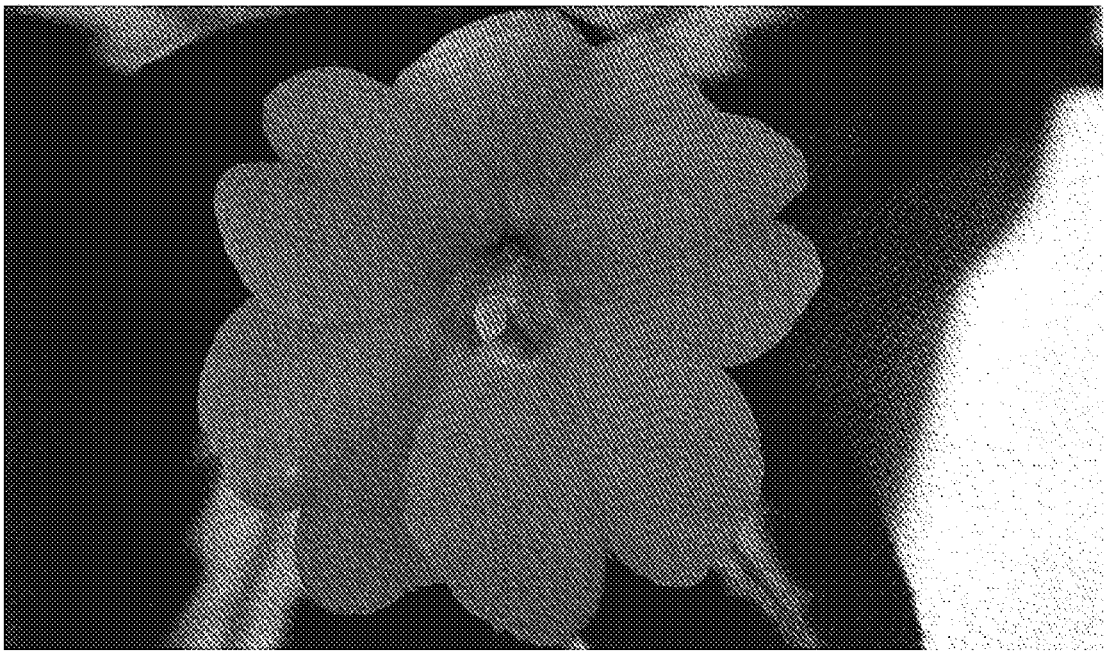
FIG. 2 shows the mature inflorescence.

The following detailed descriptions set forth the distinctive characteristics of 'SAKIMP015'. The data which define these characteristics were collected from asexual reproductions carried out in Salinas, Calif. The plant history was taken on plants grown for about five months from propagation by terminal cuttings under greenhouse conditions. Color references are primarily to the R.H.S. Colour Chart of The Royal Horticultural Society of London (R.H.S.), $4^{th}$ edition (2001). Anatomic labels are from The Cambridge Illustrated Glossary of Botanical Terms, by M. Hickey and C. King, Cambridge University Press.

DETAILED BOTANICAL DESCRIPTION

Classification:
*Family.*—Balsaminaceae.
*Botanical.—Impatiens×hybrida.*
*Common name.—Impatiens.*

Parentage:
*Female parent.*—'NC-1H1' an unpatented proprietary light-orange flowered *Impatiens* plant.
*Male parent.*—'NG-01H-9B', an unpatented proprietary pink-lilac flowered *Impatiens* plant.

Growth:
*Time to produce a rooted cutting.*—The terminal 1.0 to 1.5 inches of an actively growing stem was excised.

The vegetative cuttings were propagated in five to six weeks. The base of each cutting was dipped for 1 to 2 seconds in a 1:9 solution of Dip 'N Grow (1 solution: 9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed.

*Environmental conditions for plant growth.*—Rooted cuttings were transplanted and grown in 6-inch plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Plants were fertilized every 2–3 days, 2 times in consecutive applications and then given one clear water application. Pots were top-dressed with a dry, slow release fertilizer containing 14% nitrogen, 14% phosphorus and 14% potassium. The typical average air temperature was 24° C.

*Time to bloom from propagation.*—6 to 8 weeks.

Plant Description:

*Habit.*—Compact, loosely branching.
*Life cycle.*—Tender perennial.
*Height.*—23.0 cm to 24.0 cm from soil line to top of foliage.
*Spread.*—40.0 cm to 42.0 cm.
*Time to produce a rooted cutting.*—4 weeks.
*Flowering requirements.*—Will flower so long as temperature is above 5° C.
*Temperature tolerance.*—Plants have been observed to continuously flower at a temperature range of 5° C. to 36° C.; plants can withstand high heat and humidity.

Branches:

*Number.*—9 total with 3 main branches.
*Length.*—3.0 cm from soil line to first node; 15.0 cm to 16.0 cm total.
*Diameter* (*main branch*).—1.0 cm.
*Color.*—RHS 187D (Greyed-Purple).

Stems:

*Length.*—4.0 cm from first to second node.
*Diameter.*—0.5 cm to 0.6 cm.
*Internode length.*—2.5 cm to 4.0 cm.
*Color.*—RHS 186A (Greyed-Purple).
*Stem description.*—Strong; circular cross-section, smooth and shiny.
*Pubescence.*—Absent.
*Anthocyanin color.*—RHS 186A (Greyed-purple).

Leaves:

*Arrangement.*—Whorled with up to 5 leaves per node, opposite if only two leaves at one node.
*Length.*—8.0 cm to 9.0 cm.
*Width.*—3.5 cm to 3.7 cm.
*Shape.*—Lanceolate, curled.
*Margin.*—Ciliate.
*Apex.*—Acuminate.
*Base.*—Attenuate.
*Texture.*—Dull; waxy.
*Color.*—Upper surface: Variegated, RHS 139A (Green) along outer edge with RHS 13D (Yellow) from inside edge to center. Lower surface: RHS 148A (Yellow-green) along outer edge with RHS 8D (Yellow) from inside edge to center.
*Fragrance.*—Absent.
*Pubescence.*—Absent.
*Venation.*—Pinnate.
*Venation color* (*both surfaces*). RHS 186B (Greyed-purple).
*Petiole.*—Length: 1.0 cm to 1.2 cm. Diameter: 0.5 cm to 0.6 cm. Color RHS 186A (Greyed-purple). Texture: Smooth, glabrous.

Flower buds:

*Shape.*—Deltoid, longitudinal cross-section.
*Length.*—1.5 cm.
*Diameter.*—1.2 cm.
*Color.*—RHS 52C (Red) with RHS 53A (Red) at edge.
*Texture.*—Glabrous.

*Inflorescence:*

*Blooming habit.*—Will flower as long as the temperature is above 5° C.
*Inflorescence type.*—Single flower with spur.
*Number of flowers per node.*—1 in bloom at one time; about 3 flower buds.
*Number of flowers per plant.*—10 in bloom.
*Lastingness of individual blooms on the plant.*—14 days.
*Fragrance.*—Absent.

Peduncles:

*Length.*—5.0 cm to 5.2 cm.
*Diameter.*—0.2 cm.
*Color.*—RHS 56D (Red).
*Texture.*—Smooth, glabrous.

Corolla:

*Shape.*—Roughly circular with 5 radial petals.
*Diameter.*—4.5 cm.
*Depth.*—0.2 cm to 0.3 cm.

Petals:

*Shape.*—Obcordate.
*Length.*—3.0cm.
*Width.*—2.8 cm.
*Apex.*—Emarginate (cleaved).
*Base.*—Attenuate.
*Margin.*—Entire.
*Texture.*—Glabrous.
*Color.*—Upper surface: RHS 41C (Red). Lower surface: RHS 52D (Red). Eye zone: RHS 53A (Red).

Spur:

*Shape.*—Tubular and curved downward.
*Color.*—RHS 56D (Red) at top and fading to RHS 145D (Yellow-green) at tip.
*Length.*—6.0 cm.
*Diameter.*—0.2 cm.

Sepals:

*Shape.*—Lanceolate.
*Number.*—Two.
*Color.*—RHS 65D (Red-purple) on inside and RHS 147C (Yellow-Green) around rim.
*Length.*—0.7 cm.
*Diameter.*—0.4 cm.
*Apex.*—Caudate.
*Base.*—Subcordate.
*Margin.*—Entire.
*Texture.*—Glabrous.

Reproductive organs:

*Stamens.*—Form: Fused; split into 4 lobes. Number: Many. Filament length: 0.4 cm. Filament color: RHS 53D (Red). Anther length: 0.4 cm. Anther color: RHS N155A (White). Pollen amount: Abundant.

Pollen color: RHS N155A (White). Pollen description: Powdery.

*Pistil.*—Number 5. Stigma color: RHS 143A (Green). Style color: RHS 143A (Green).

*Ovary arrangement.*—Parietal.

*Ovary surface color.*—RHS 144B (Yellow-green).

Fruit and Seed set: No seed set observed.

Disease and insect resistance: No particular resistance or susceptibility has been observed.

COMPARISON WITH PARENTAL AND COMMERCIAL CULTIVARS

'SAKIMP015' is similar to the female parent 'NG-01H-9B' and the male parent 'NC-1H1', however, there are differences as listed in the table below:

TABLE 1

Comparison of Characteristics between 'SAKIMP015' and parental cultivars

| Characteristic | 'SAKIMP015' | Male Parent 'NG-01H-9B' | Female Parent 'NC-1H1' |
|---|---|---|---|
| Flower color | Pinkish-Orange | Pink-Lilac | Light Orange |
| Flower size | Small | Small | Medium |
| Plant growth habit | Compact | Mounding | Mounding |

'SAKIMP015' is similar to the commercial *Impatiens* variety 'Misato FG2' (U.S. Plant Pat. No. 17,663) (known commercially as 'SunPatiens Orange') however, there are differences as listed in the table below:

TABLE 2

Comparison of Characteristics between 'SAKIMP015' and 'Misato FG2'

| Characteristic | 'SAKIMP015' | 'Misato FG2' |
|---|---|---|
| Growth habit | Compact | Upright |
| Petal color, upper surface | RHS 41C (Red) | RHS N30C (Orange-Red) |
| Spur color | RHS 56D (Red) at top fading to RHS 145D (Yellow-Green) at tip | RHS 63A (Red-Purple) at top fading to RHS 62D (Red-Purple) at tip |
| Leaf color, upper surface | Variegated with RHS 139A (Green) along outer edge and RHS 13D (Yellow) from inside edge to center of leaf | RHS 136A (Green) |

I claim:

1. A new and distinct cultivar of New Guinea *Impatiens* plant as shown and described herein.

* * * * *